(12) United States Patent
Grossi

(10) Patent No.: US 6,358,200 B1
(45) Date of Patent: Mar. 19, 2002

(54) CONTINUOUS FLOW RESECTOSCOPE WITH SINGLE TUBE SHEATH ASSEMBLY AND ROTATABLE CONNECTION

(75) Inventor: Benedetto Grossi, Stamford, CT (US)

(73) Assignee: Circon Corporation, Goleta, CA (US)

( * ) Notice: Subject to any disclaimer, the term of this patent is extended or adjusted under 35 U.S.C. 154(b) by 0 days.

(21) Appl. No.: 09/387,993

(22) Filed: Sep. 1, 1999

(51) Int. Cl.[7] .................................................. A61B 1/12
(52) U.S. Cl. ........................ 600/156; 600/121; 600/128
(58) Field of Search ................................. 600/121, 153, 600/156, 158, 128

(56) References Cited

U.S. PATENT DOCUMENTS

| | | | | |
|---|---|---|---|---|
| 3,835,842 A | * | 9/1974 | Iglesias | ........................ 128/7 |
| 3,850,162 A | * | 11/1974 | Iglesias | ........................ 128/6 |
| 3,850,175 A | * | 11/1974 | Iglesias | ................. 128/303.15 |
| 4,423,727 A | * | 1/1984 | Widran et al. | ......... 128/303.15 |
| 4,726,370 A | * | 2/1988 | Karasawa et al. | ..... 128/303.15 |
| 4,920,961 A | | 5/1990 | Grossi et al. | .................. 606/14 |
| 5,131,382 A | * | 7/1992 | Meyer | ............................ 128/6 |
| 5,486,155 A | * | 1/1996 | Muller et al. | ................ 600/137 |
| 5,807,240 A | * | 9/1998 | Muller et al. | ................ 600/135 |
| 5,857,962 A | | 1/1999 | Bracci et al. | ................ 600/105 |

* cited by examiner

Primary Examiner—Linda C. M. Dvorak
Assistant Examiner—Jocelyn Ram
(74) Attorney, Agent, or Firm—Perman & Green, LLP

(57) ABSTRACT

A continuous flow endoscope comprising a working element and an outer sheath assembly. The working element comprises a frame including a telescope guide tube and a fluid passage through the frame and into the telescope guide tube. The outer sheath assembly is connected to the frame. The outer sheath assembly comprises an outer tube located around a portion of the telescope guide tube. The outer tube and the telescope guide tube form a fluid outflow conduit therebetween along a majority of the length of the outer tube.

11 Claims, 6 Drawing Sheets

CONTINUOUS FLOW RESECTOSCOPE WITH SINGLE TUBE SHEATH ASSEMBLY AND ROTATABLE CONNECTION

BACKGROUND OF THE INVENTION

1. Field of the Invention

The present invention relates to medical instruments and, more particularly, to an endoscope.

2. Prior Art

U.S. Pat. No. 5,807,240 discloses a continuous flow resectoscope with a sheath assembly having two tubes; an inner tube and an outer tube. U.S. Pat. No. 5,486,155 discloses a rotatable endoscope sheath. U.S. Pat. No. 5,857,962 discloses a resectoscope with a movable actuator assembly. A problem with prior art continuous flow endoscopes is that smaller diameter shafts are desirable, but reducing the diameter of a shaft causes problems regarding sufficient flow of fluid into and out of the patient through the shaft. Another problem is that it is desirable to use existing telescopes, thus, making a reduction in shaft diameter cause fluid flow problems.

SUMMARY OF THE INVENTION

In accordance with one embodiment of the present invention, a continuous flow endoscope is provided comprising a working element and an outer sheath assembly. The working element comprises a frame including a telescope guide tube and a fluid passage through the frame and into the telescope guide tube. The outer sheath assembly is connected to the frame. The outer sheath assembly comprises an outer tube located around a portion of the telescope guide tube. The outer tube and the telescope guide tube form a fluid outflow conduit therebetween along a majority of the length of the outer tube.

In accordance with another embodiment of the present invention, an endoscope working element is provided comprising a frame and a movable portion. The frame includes a telescope guide tube. The movable portion is movably mounted to the frame. The telescope guide tube has a first cross-sectional shape along a majority of a length of the guide tube and a second different cross-sectional shape along a front end section of the guide tube.

In accordance with another embodiment of the present invention, a continuous flow or non-continuous flow endoscope outer sheath assembly is provided comprising a tube, a connector and an insulating tip. The connector is located at a rear end of the tube. The connector comprises a first mount for attaching a first fluid conduit to the connector. The insulating tip is directly connected to the front end of the tube.

In accordance with another embodiment of the present invention, a continuous flow endoscope is provided comprising a working element and a sheath assembly. The working element comprises a frame and a rotatable sheath connector connected directly to the frame. The sheath assembly is connected to the working element. The sheath assembly comprises a rear end connector directly connected to the rotatable sheath connector. The rear end connector comprises two fluid conduit mounts for attaching two fluid conduits to the outer sheath assembly. The working element and the sheath assembly are directly rotatably connected to each other by the rotatable sheath connector.

In accordance with another embodiment of the present invention, a non-continuous flow endoscope is provided comprising a working element comprising a frame and a rotatable sheath connector connected directly to the frame, the frame comprising an inner tube; and a sheath assembly connected to the working element. The sheath assembly comprises an outer tube and a rear end connector directly connected to the rotatable sheath connector. The rear end connector comprises a fluid conduit mount for attaching a fluid conduit to the outer sheath assembly. The fluid conduit mount has a fluid flow passage which communicates with fluid flow passages along both the inner tube and the outer tube to a distal end of the endoscope. The working element and the sheath assembly are directly rotatably connected to each other by the rotatable sheath connector.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENT

Figure 1:
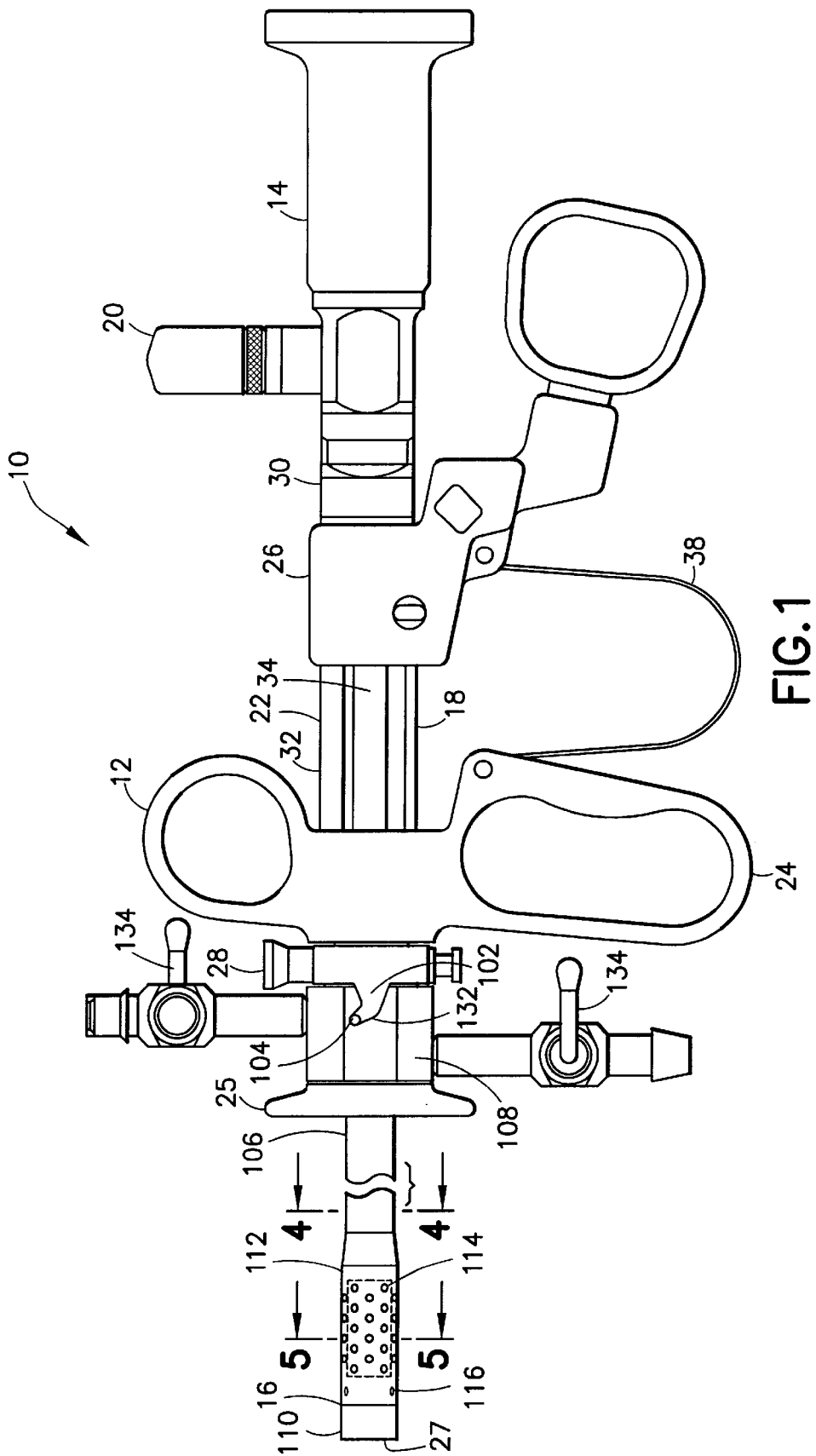
FIG. 1 is an elevational side view of a resectoscope incorporating features of the present invention.

Referring to FIG. 1, there is shown an elevational side view of a resectoscope 10 incorporating features of the present invention. Although the present invention will be described with reference to the embodiments shown in the drawings, it should be understood that the present invention can be embodied in many alternate forms of embodiments. In addition, any suitable size, shape or type of elements or materials could be used. Although the present invention is being described with reference to a resectoscope, features of the present invention could be used with any suitable type of endoscope.

The resectoscope 10 generally comprises a working element 12, a telescope 14, a sheath assembly 16 and a throughput device 18. The throughput device is a tool, such as an electrode or a fiber optic laser guide. The telescope 14, in the embodiment shown is a U.S.A. ELITE SYSTEM telescope. U.S.A. ELITE SYSTEM is a trademark of Circon Corporation of Goleta, California. The telescope 14 is removably mounted to the working element 12, and has a connector 20 for connecting fiber optics in the telescope with a light source by means of a flexible light transmitting cable (not shown). The telescope 14 is well known in the art. In alternate embodiments, any suitable type of telescope and/or throughput device could be used.

Figure 1A:
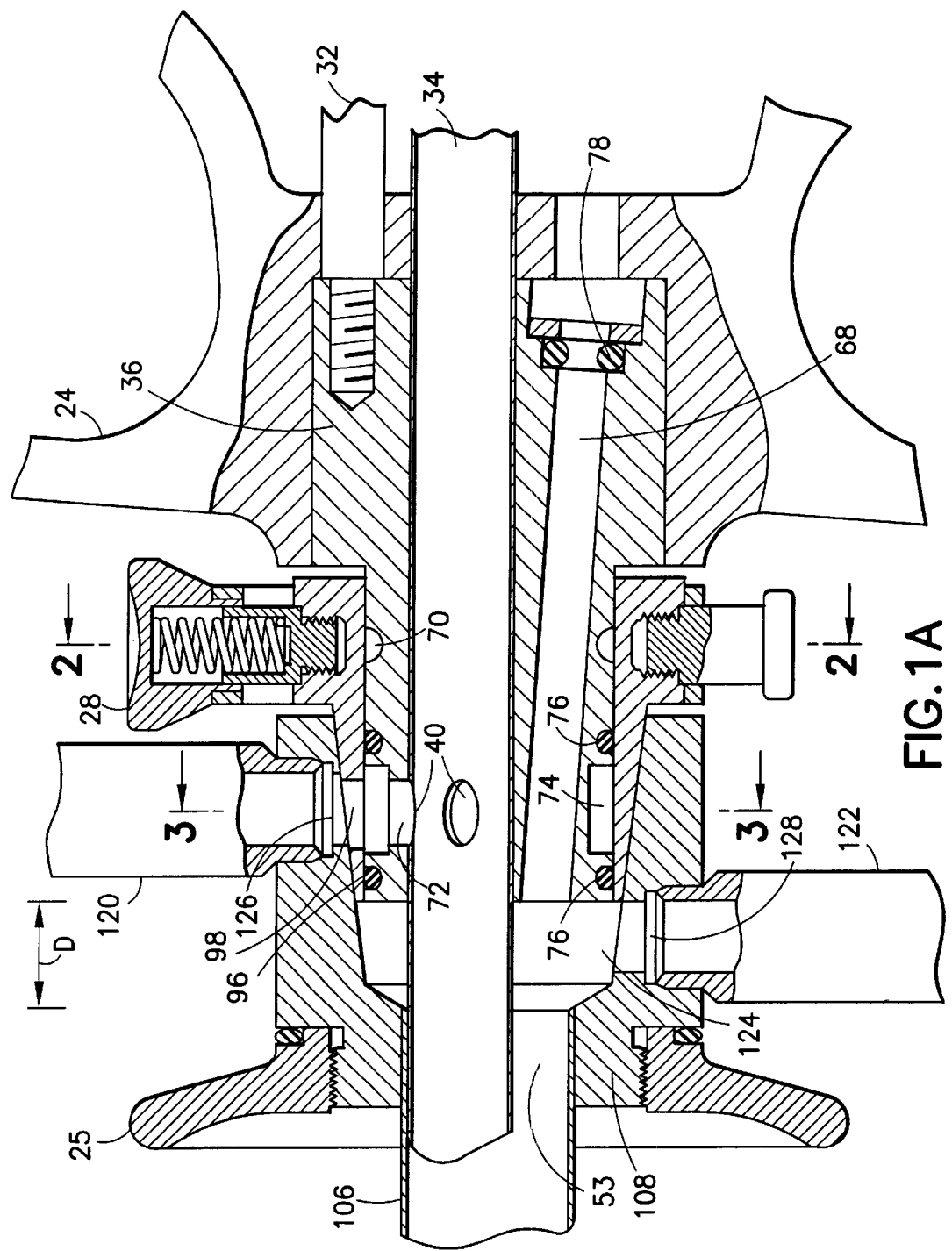
FIG. 1A is an enlarged partial cross-sectional view of a portion of the resectoscope shown in FIG. 1.

The working element 12 generally comprises a frame 22, a movable portion 26, and a latch assembly 28. Referring also to FIG. 1A, the frame 22 generally comprises a front handle 24, a rear section 30, a guide bar 32, a telescope guide tube 34 and a front section 36. The front and rear sections 36, 30 are connected to each other by the guide bar 32 and the telescope guide tube 34. The movable portion 26 is slidingly mounted on the guide bar 32 and the telescope guide tube 34 between the rear position shown in FIG. 1 and a forward position against the rear end of the front handle 24. A spring 38 biases the movable portion 26 in the rear position. Any suitable movable portion could be provided, such as described in U.S. Pat. No. 5,857,962 which is hereby incorporated by reference in its entirety. A non-spring loaded movable portion could also be provided, such as having a crank. The telescope guide tube 34 extends through the front section 36 to a front end of the resectoscope. The guide tube 34 includes three fluid entry holes 40 at the front section 36. However, any suitable fluid entry could be provided in the tube 34 at the front section 36. The rear end of the tube 34 is open for introduction and removal of the telescope 14. The rear section 30 preferably comprises a seal (not shown) to seal the rear end of the tube 34 with the telescope 14.

Figure 4:
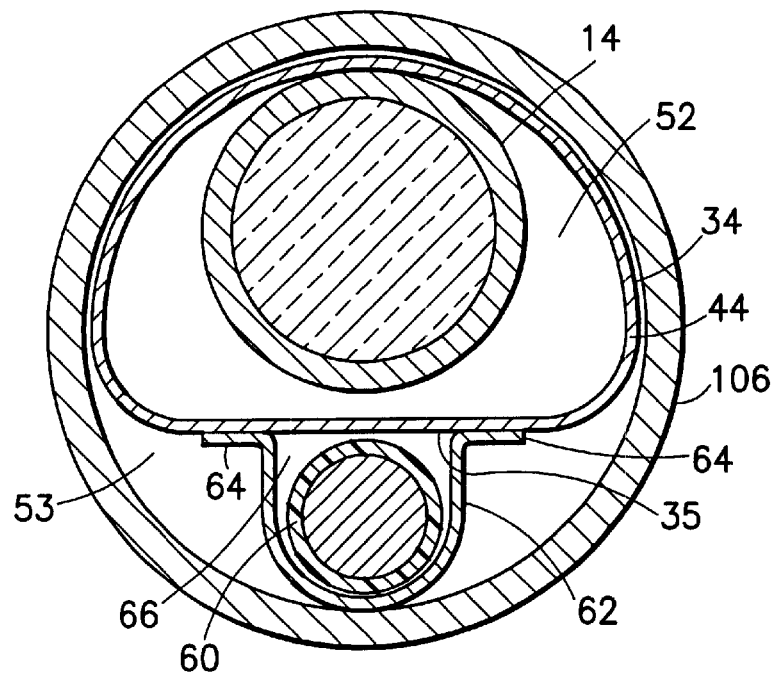
FIG. 4 is a cross-sectional view of the resectoscope shown in FIG. 1 taken along line 4—4.
Figure 5:
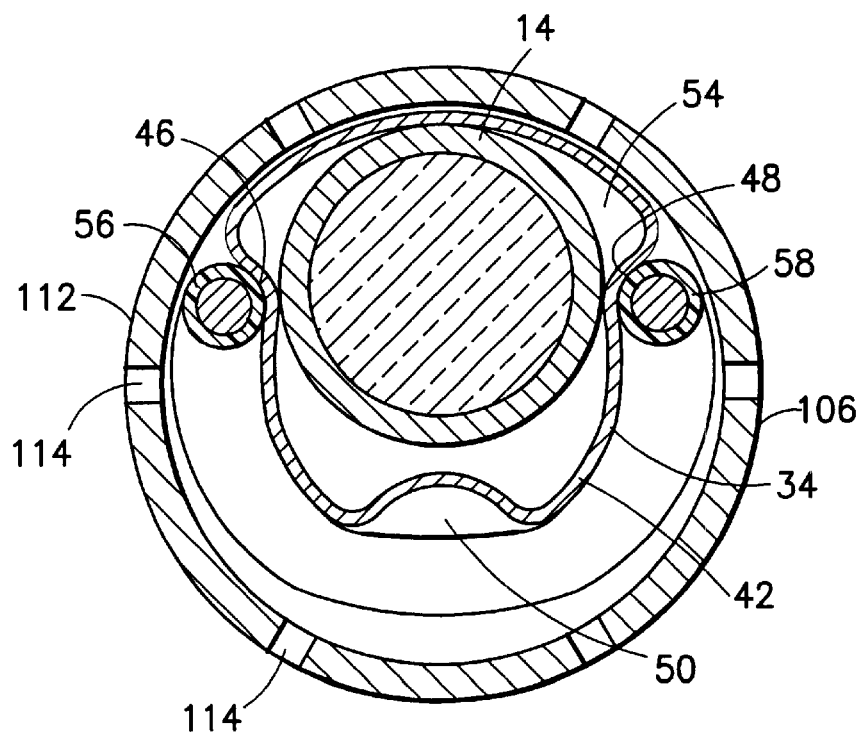
FIG. 5 is a cross-sectional view of the resectoscope shown in FIG. 1 taken along line 5—5.

Referring also to FIGS. 2–5, the telescope guide tube 34 is provided with a non-uniform cross-sectional shape along its length. The tube 34 has a front section 42 and a section 44. The section 44 preferably extends at least from the fluid entry holes 40 to the front section 42. In a preferred embodiment the section 44 also extends to the rear section 30. However, the tube 34 could have a different cross-sectional shape rearward from the front section 36. In the embodiment shown, the section 44 has a general D-shaped cross-section as best seen in FIG. 4. However, any suitable shape could be provided. The front section 42 as best seen in FIG. 5, on the other hand, comprises two concave recesses 46, 48 on opposite lateral sides and a bottom recess 50. However, the front section 42 could be provided with any suitable cross-sectional shape. In a preferred embodiment, the cross-sectional area 52 defined within the section 44 is larger than the cross-sectional area 54 defined within the front section 42. Preferably, the elongate shaft of the telescope fits snuggly against the interior side walls of the tube 34 at the front section 42 proximate the concave recesses 46, 48 and the top side of the tube 34. The concave recesses 46, 48 form guide stabilizers for slidingly capturing arms 56, 58 of the electrode 18 at the front end of the electrode. Thus, the electrode 18 does not need its own separate stabilizer as in the prior art. The stabilization function is integrated into the front section 42. The bottom recess 50 also functions as a guide stabilizer for the main shaft 60 of the electrode 18 as the electrode is longitudinally extended and retracted when the movable portion 26 is moved. Because the tube 34 is preferably a one-piece metal member, there is preferably a smooth transition between the two sections 42, 44.

The frame 22 also preferably comprises an elongate electrode guide member 62. In this embodiment the guide member 62 is fixedly attached directly to the bottom flat side 36 of the telescope guide tube section 44 along a majority of the length of the tube section 44 between the front section 36 and the front section 42. The guide member 62 preferably has a general U-shaped cross-section with its ends 64 attached to the side 35. The guide member 62 and side 35 of the tube 34, thus, form an electrode passage 66 for a portion of the main shaft 60 of the electrode 18. Hence, the electrode passage 66 and area 52 share a common wall at side 35. This common wall configuration helps to reduce the cross-sectional size of the instrument because it is smaller than a double wall. However, any suitable type or shape of guide member or members could be provided.

Referring now to FIGS. 1, 1A, 2B and 3, the front section 36 comprises an electrode guide channel 68. An annular bearing channel 70, fluid conduits 72 with an annular groove 74 and seals 76, such as O-rings. An O-ring seal 78 is located in the electrode guide channel 68 for sealing off the rear end of the channel 68 with the electrode 18. Ball bearings 80 are located in the annular bearing channel 70 to rotatably mount the connector 28 to the front section 36. The fluid conduits 72 are aligned with the holes 40 in the telescope guide tube 34. The seals 76 make a sealing engagement between the front section 36 and the connector 28 around the annular groove 74 into the conduits 72.

Figure 2:
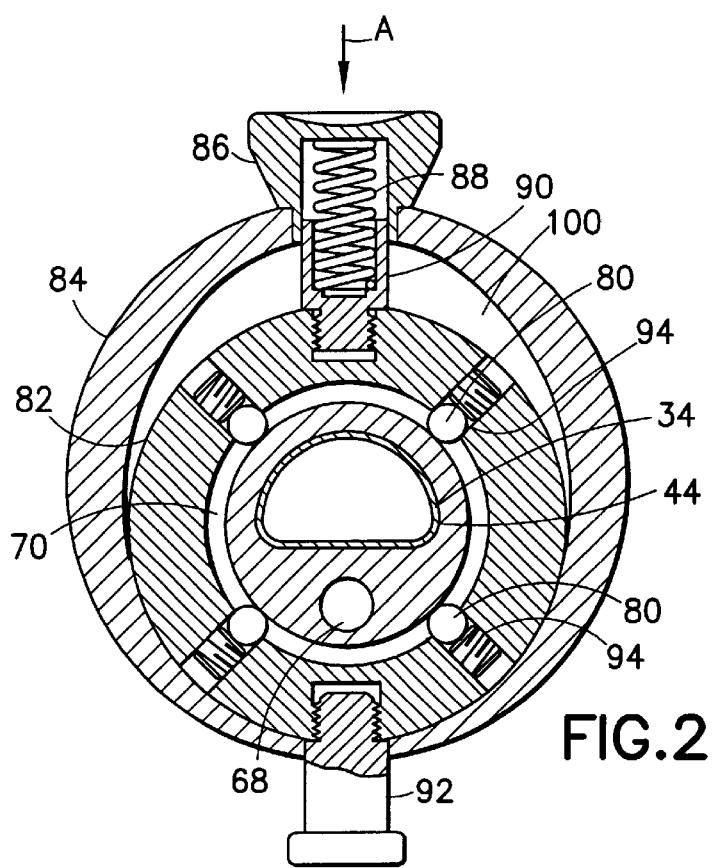
FIG. 2 is a cross-sectional view of the resectoscope shown in FIG. 1A taken along line 2—2.
Figure 3:
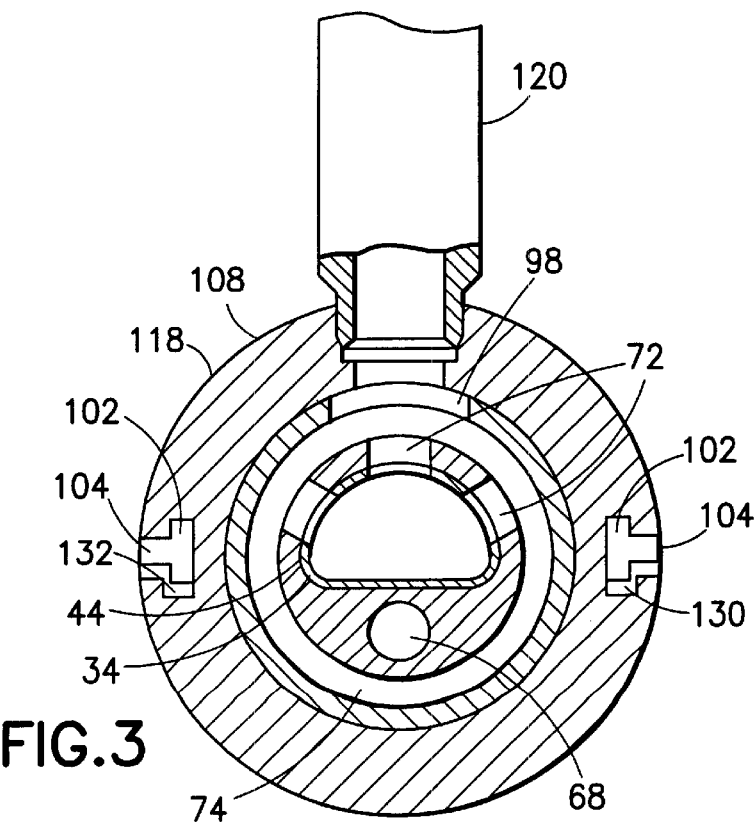
FIG. 3 is a cross-sectional view of the resectoscope shown in FIG. 1A taken along line 3—3.

The connector 28 generally comprises a first ring-shaped member 82, a second ring shaped member 84, a plunger 86, a spring 88, and two guides 90, 92. The two guides 90, 92 are fixedly attached to the inner member 82. The inner member 82 is rotatably connected to the front section 36 of the frame 22 by the bearings 80. The interaction of the bearings 80 with the bearing channel 70 and the bearing seating holes 94 in the inner member 82 prevents the inner member 82 from longitudinally moving along the length of the front section 36. The seals 76 make a sealing engagement with the underside of the inner member 82. The inner member 82 also comprises a front cone shaped section 96 with a fluid hole 98 therethrough. The fluid hole 98 is aligned with the annular groove 74 in the front section 36. The outer member 84 is located around the rear end of the inner member 82. The plunger 86 is attached to the outer member 84. The outer member 84 has holes through it with the two guides 90, 92 located in the holes. The spring 88 is located between the guide 90 and the plunger 86 to bias the outer member 84 in an upward direction relative to the inner member 82 as shown in FIG. 2. However, the area 100 inside the outer member 84 is larger than the inner member 82 such that the outer member can be moved relative to the inner member 82, as indicated by arrow A, with the spring 88 being compressed and the outer member 84 sliding on the guides 90, 92. The outer member 84 comprises two forward extending lateral side arms 102 with outwardly extending latch pins 104 (see FIG. 1) on opposite sides of the outer member 84. When the outer member 84 is moved up and down on the inner member 82, the pins 104 are moved up and down. The spring 88 returns the outer member 84 and pins 104 to an upward position when the plunger 86 is released by the user.

The outer sheath assembly 16 generally comprises a single tube 106, a single connector 108 at the rear end of the tube 106, and an insulating tip 110 at the front end of the tube 106. The tube 106 forms an outer tube for the shaft. The tube 106 is preferably comprised of metal with a general circular ring shaped cross-section. The front end 112 of the tube 106 is slightly enlarged with holes 114 through the side wall of the tube. The insulating tip 110 is preferably comprised of dielectric material such as ceramic. The insulating tip 110 is generally ring shaped and extends into the front end of the tube 106. The tip 110 is preferably glued or bonded and also mechanically retained to the tube 106 by dimples 116. The connector 108 generally comprises a frame 118 and two fluid conduit mounts 120, 122. The frame 118 includes a cone shaped receiving area 124 extending into its rear end, two areas 126, 128 for mounting the fluid mounts 120, 122 for access into the receiving area 124, and two side latch areas 130, 132 for receiving the arms 102 and pins 104 of the connector 28. The two fluid mounts 120, 122 each include a stopcock 134.

Interaction between the two connectors 28, 108 is similar to that described in U.S. Pat. No. 4,920,961 which is hereby incorporated by reference in its entirety. When the two connectors 28, 108 are connected to each other the fluid flow area 126 and fluid inlet mount 120 are aligned with the fluid hole 98 into the annular channel 74. Thus, fluid can flow from a conduit connected to the fluid inlet mount 120 into the interior of the telescope guide tube 34. Fluid and debris can flow out the fluid outlet mount 122. Referring now to FIGS. 4 and 5, the areas 52, 54 between the outside of the telescope shaft and the inside of the telescope guide tube 34 form a fluid inflow channel or passage to the distal end of the resectoscope. The area 53 between the outside surface of the telescope guide tube 34 and the inside of the outer sheath tube 106 forms a fluid outflow channel or passage. Thus, with the present invention a continuous flow resectoscope is provided without the sheath assembly having two tubes; an inner tube and an outer tube. Instead, the sheath assembly 16 only comprises the outer tube 106 and the telescope guide tube 34 of the frame 22 is used to perform the function of the prior art sheath assembly inner tube. This allows the cross-sectional area of the resectoscope shaft to be reduced because of the elimination of the sheath assembly inner tube. In addition, the distance D between the front end of the front section 36 of the frame 22 and the rear end of the outer sheath tube 106 is smaller than in the prior art because of the elimination of the prior art inner sheath assembly and its rear connector. The outer sheath assembly connector 108 is directly connected to the connector 28 on the frame 22 without an intermediate connector therebetween. This allows the sheath assembly 16 to be longer than in the prior art while still allowing same length electrodes 18 to be used as in the prior art resectoscopes; the electrodes merely being manufactured without the prior art stabilizer being attached. The extra working length of the resectoscopes, from the washer 25 to the distal tip 27 could be increased by about 0.75 inch while using the same length telescope and electrodes as in the prior art. A longer length resectoscope shaft can be easier to use; especially with obese patients.

The most expensive part of the resectoscope is the telescope 14. Therefore, in designing a new resectoscope it is desirable to have the new resectoscope be able to use a current telescope that the user already owns. Two sizes of telescopes include 4 mm and 3 mm sizes.,the 4 mm size telescope is presently used in a continuous flow resectoscope having resectoscope sheath outer diameters of about 25 French and 27 French. Such prior art resectoscopes use sheath assemblies that have an inner tube and an outer tube. With the present invention, the prior art 4 mm telescope can be used with the sheath assembly 16 having an outer diameter of only about 22 French. The flow of fluid through the areas 52, 53, 54 will be about 90% or higher as provided in the prior art 25/27 French design which should be sufficient to provide good removal of blood and debris from the field of view of the user. The relative percentage would be much lower if the prior art inner sheath tube was still present. With a 3 mm telescope and the present invention the outer diameter of resectoscope shaft could be reduced to about 20 French while retaining about 90% of the flow rate Q as in the prior art. The smaller outer diameter of the resectoscope shaft can be easier for the user to insert and less painful to the patient. In order to assist in clearing the field of view of the user with the reduced fluid flow rate, the reduced cross-sectional flow area 54 at the front end of the telescope guide tube 34 causes an increase in velocity of the inflowing fluid as the fluid is discharged from the front end of the resectoscope. This increased velocity fluid at the distal tip of the telescope 14 clears away blood and debris from the user's field of view more quickly than in the prior art even with the 10% reduction in the incoming fluid flow rate. The present invention also moves the inflow closer to the end of the telescope than in the prior art to increase the cleaning of the field of view.

The present invention also overcomes a problem in the prior art in regard to the insulating tip. In prior art continuous flow resectoscopes an insulting tip made of ceramic material was provided at the distal end of the inner sheath. When inserting the inner sheath into and through the outer sheath torque applied to the inner sheath resulted in the insulating tip cracking. Pieces of the tip could break off inside the patient. With the present invention, the insulating tip can be mounted directly to the outer sheath. Therefore, this eliminates torque forces on the insulating tip, and resultant cracking, that existed in the inner/outer sheath assembly in the prior art.

Figure 6:
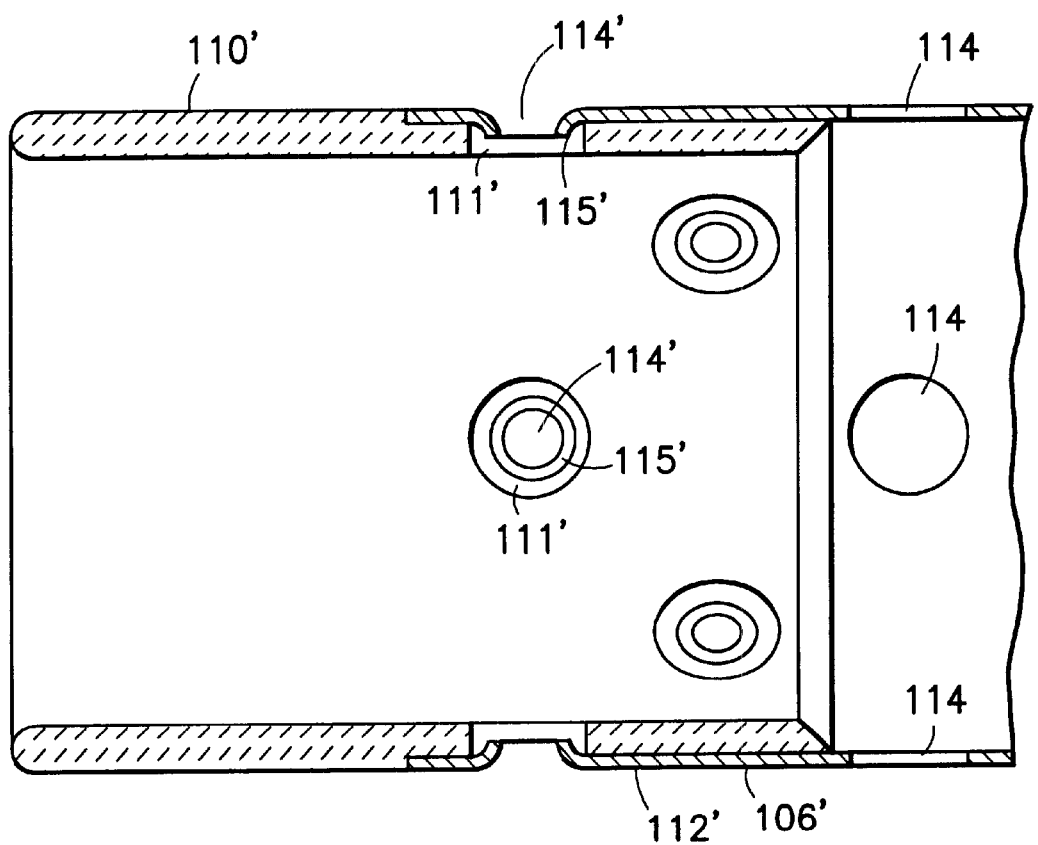
FIG. 6 is a cross-sectional view of an alternate embodiment of the front end of the outer sheath assembly.

Referring also to FIG. 6 an alternate embodiment of the front end 112' of the outer sheath is shown. In this embodiment the tube 106' includes the holes 114 and additional holes 114'. The holes 114' include indented sections 115'. The insulating tip 110' includes holes 111'. The indented sections 115' project into the holes 111' to mechanically attach the tube 106' to the tip 110' and, the holes 114' and 111' also function, similar to holes 114, as outlets through the side of the outer sheath for the outflow of fluid and debris from inside the patient. Hence, the resectoscope can have a larger combined area of outflow side openings at its distal end than in the prior art. In addition to the interlocking of indented sections 115' into the holes 111', the connection of the tip 110' to the tube 106' also preferably comprises a bonding or adhesive attachment. The present invention could also include an outflow channel through the insulated tip as disclosed in U.S. Pat. No. 5,807,240 which is hereby incorporated by reference in its entirety.

The present invention also provides another advantage. In the prior art continuous flow resectoscopes, such as described in U.S. Pat. Nos. 4,920,961, 5,486,155 and 5,807,240, the sheath assembly comprises a movable latch as well as the working element having a movable latch. With the present invention, the continuous flow resectoscope comprises only one movable latch 28; not two as in the prior art continuous flow resectoscopes. Therefore, the continuous flow resectoscope of the present invention is less expensive to manufacture than the prior art and is also less complicated to clean.

The present invention also provides another advantage. Even though the outside diameter of the outer sheath 16 is being reduced to about 22 French along most of its length, the resectoscope 10 is still able to use electrodes (less an electrode stabilizer) which were originally designed for the 25 French instrument. These 25 French electrodes have a working end at their distal tips that are larger than electrodes designed for a 22 French instrument having an inner/outer sheath design. The 25 French electrode can remove more tissue in a single swipe then a 22 French electrode having a smaller working end. Therefore, the present invention also allows the user to remove tissue faster than use of a conventional design. Features of the present invention could also be used with a non-continuous flow outer sheath with a single fluid mount feeding fluid into both areas 52, 53.

Figure 1B:
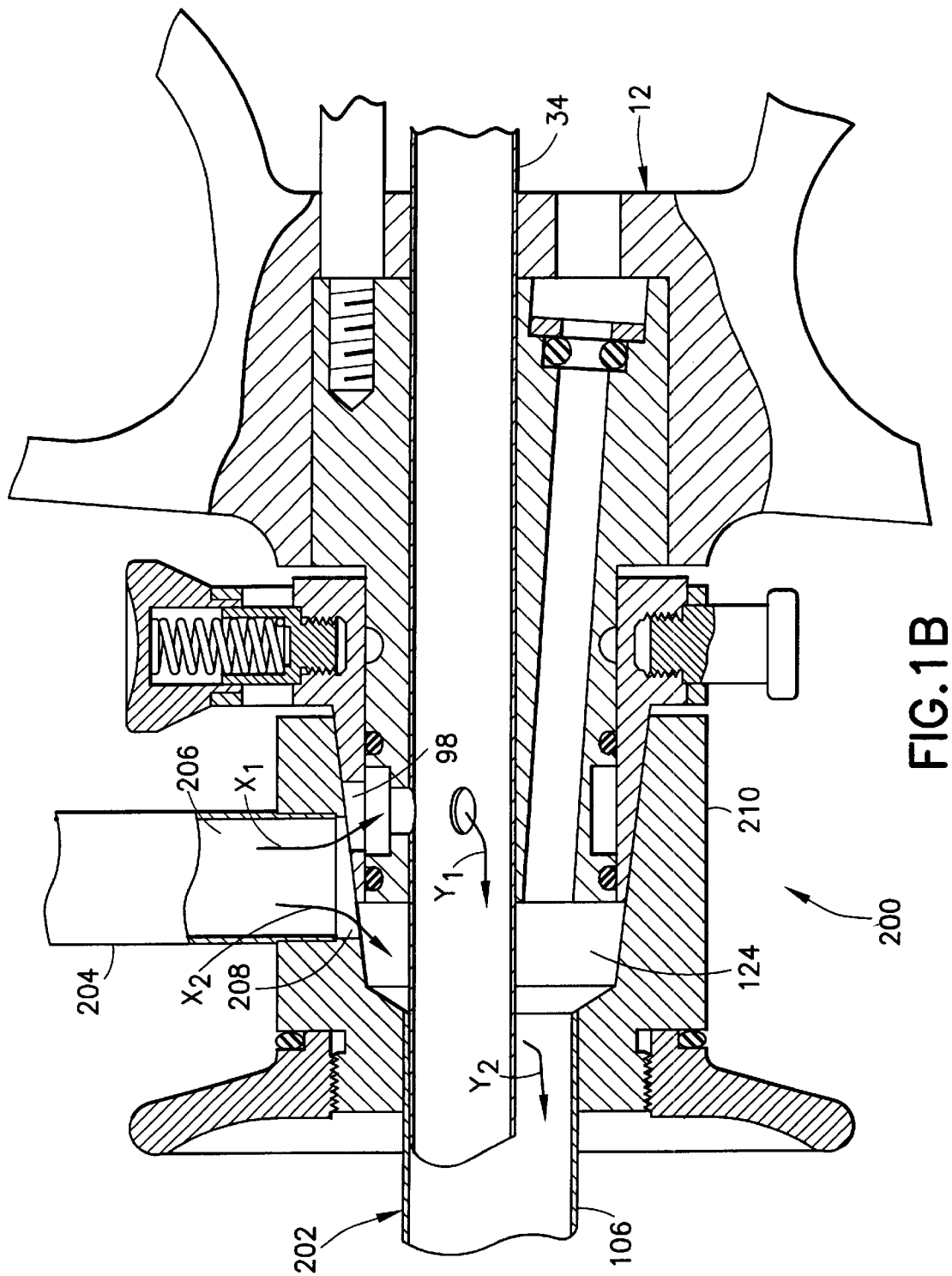
FIG. 1B is an enlarged partial cross-sectional view of a portion of an alternate embodiment of the resectoscope as shown in FIG. 1A.

FIG. 1B shows an alternate embodiment of the present invention. In this embodiment the endoscope 200 comprises the working element 12, the telescope 14 (not shown in this view for the sake of clarity), and a single sheath assembly 202. The sheath assembly 202 is substantially similar to the sheath assembly 16, but comprises a single fluid conduit mount 204 rather than two fluid conduit mounts. The fluid flow passages 206, 208 through the respective mount 204 and the rear end connector frame 210 extend into areas 98 and 124. As indicated by arrows $X_1$ and $X_2$ fluid from the mount 204 can flow into areas 98 and 124. Thus, fluid from the mount 204 can flow into both tubes 34, 106 as indicated by arrows $Y_1$ and $Y_2$ to the distal end of the endoscope. This type of embodiment can be used for a non-continuous flow resectoscope.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A continuous flow endoscope comprising:
    a working element comprising a frame, the frame including a telescope guide tube having a varying cross-sectional shape along its length and a fluid passage through the frame and into the telescope guide tube; and
    an outer sheath assembly connected to the frame, the outer sheath assembly comprising an outer tube located around a portion of the telescope guide tube, wherein the outer tube and the telescope guide tube form a fluid outflow conduit therebetween along a majority of the length of the outer tube.

2. An endoscope as in claim 1 further comprising a telescope extending through the telescope guide tube, wherein the telescope and the guide tube form a fluid inflow conduit therebetween.

3. An endoscope as in claim 1 wherein the telescope guide tube comprises a first cross-sectional shape along a majority of a length of the guide tube and a second different cross-sectional shape at a front end section of the guide tube.

4. An endoscope as in claim 3 wherein a cross-sectional area inside the guide tube along the majority of the length is larger than a cross-sectional area inside the guide tube at the front end section.

5. An endoscope as in claim 1 wherein the working element further comprises a connector for directly connecting the working element to the outer sheath assembly.

6. An endoscope as in claim 5 wherein the connector is rotatable such that the outer sheath assembly can rotate relative to the guide tube.

7. An endoscope as in claim 1 wherein the outer sheath assembly further comprises an insulating tip mounted to a front end of the outer tube.

8. An endoscope as in claim 7 wherein the insulating tip has holes through a side wall aligned with holes through a side wall of the outer tube.

9. An endoscope as in claim 1 wherein the telescope guide tube has concave indentations on opposite exterior sides at a front end section of the guide tube for receiving and guiding portions of an electrode.

10. An endoscope as in claim 1 wherein the frame further comprises an elongate electrode guide attached directly to the telescope guide tube.

11. An endoscope as in claim 10 wherein the telescope guide tube defines an electrode passage with the electrode guide along the length of the electrode guide.

* * * * *